United States Patent
Manzer et al.

(10) Patent No.: US 6,353,035 B2
(45) Date of Patent: Mar. 5, 2002

(54) FISCHER-TROPSCH PROCESSES USING XEROGEL AND AEROGEL CATALYSTS BY DESTABILIZING AQUEOUS COLLOIDS

(75) Inventors: Leo E. Manzer, Wilmington, DE (US); Kostantinos Kourtakis, Swedesboro, NJ (US)

(73) Assignee: Conoco Inc., Houston, TX (US)

( * ) Notice: Subject to any disclaimer, the term of this patent is extended or adjusted under 35 U.S.C. 154(b) by 0 days.

(21) Appl. No.: 09/789,987

(22) Filed: Feb. 21, 2001

Related U.S. Application Data

(62) Division of application No. 09/377,008, filed on Aug. 18, 1999, now Pat. No. 6,235,677.
(60) Provisional application No. 60/097,192, filed on Aug. 20, 1998, provisional application No. 60/097,193, filed on Aug. 20, 1998, and provisional application No. 60/097,194, filed on Aug. 20, 1998.

(51) Int. Cl.$^7$ .............................................. C07C 27/06
(52) U.S. Cl. ....................... 518/700; 518/715; 518/719; 518/721; 502/232
(58) Field of Search ................. 518/700, 715, 518/719, 721; 502/232

(56) References Cited

U.S. PATENT DOCUMENTS

| | | | |
|---|---|---|---|
| 3,963,646 A | 6/1976 | Teichner et al. | 502/235 |
| 3,977,993 A | 8/1976 | Lynch | 252/317 |
| 4,191,637 A | 3/1980 | Light et al. | 208/139 |
| 4,422,960 A | 12/1983 | Shiroto | 502/208 |
| 4,469,814 A | 9/1984 | Robinson et al. | 502/263 |
| 4,469,816 A | 9/1984 | Armor et al. | 502/333 |
| 4,619,908 A | 10/1986 | Cheng et al. | 502/214 |
| 4,717,708 A | 1/1988 | Cheng et al. | 502/233 |
| 5,021,385 A | 6/1991 | Daly et al. | 502/211 |
| 5,080,872 A | 1/1992 | Jezl et al. | 422/201 |
| 5,134,109 A | 7/1992 | Uchiyama et al. | 502/324 |
| 5,302,622 A | 4/1994 | Chaumette et al. | 518/713 |
| 5,395,805 A | 3/1995 | Droege et al. | 501/72 |
| 5,480,852 A | 1/1996 | Mueller et al. | 502/210 |
| 5,538,931 A * | 7/1996 | Heinrichs et al. | 502/234 |
| 5,647,962 A | 7/1997 | Jansen et al. | 203/57 |
| 5,658,497 A | 8/1997 | Kumar et al. | 252/373 |
| 5,718,878 A | 2/1998 | Zheng | 423/610 |
| 5,958,363 A | 9/1999 | Coronado | 423/592 |

FOREIGN PATENT DOCUMENTS

| | | |
|---|---|---|
| GB | 2258414 | 2/1993 |

OTHER PUBLICATIONS

Xiaoding Xu, and J. A. Moulijn, "Transformation of a Structured Carrier into Structured Catalyst", Structured Catalysts and Reactors, Chapter 21, 599–615 (1998).
PCT International Search Report, International App. No. PCT/US99/18896, dated Oct. 26, 1999.

\* cited by examiner

Primary Examiner—Elizabeth D. Wood
(74) Attorney, Agent, or Firm—Conley, Rose & Tayon, P

(57) ABSTRACT

A process is disclosed for producing hydrocarbons by contacting a feed stream comprising hydrogen and carbon monoxide with a catalyst in a reaction zone maintained at conversion-promoting conditions effective to produce an effluent stream comprising hydrocarbons. The process is characterized by using a catalyst prepared by a method involving (1) forming a catalyst gel by destabilizing an aqueous colloid comprising (a) at least one catalytic metal for Fischer-Tropsch reactions (e.g., iron, cobalt, nickel and/or ruthenium), (b) colloidal cerium oxide, zirconium oxide, titanium oxide and/or aluminum oxide, and optionally (c) $Al(OR)_3$, $Si(OR)_4$, $Ti(OR)_4$ and/or $Zr(OR)_4$ where each R is an alkyl group having from 1 to 6 carbon atoms; and (2) drying the gel.

22 Claims, No Drawings

FISCHER-TROPSCH PROCESSES USING XEROGEL AND AEROGEL CATALYSTS BY DESTABILIZING AQUEOUS COLLOIDS

CROSS-REFERENCE TO RELATED APPLICATIONS

This application is a divisional of U.S. Ser. No. 09/377,008 filed Aug. 18, 1999 and now U.S. Pat. No. 6,235,677, which claims the benefit of U.S. provisional patent application Ser. No. 60/097,192, filed Aug. 20, 1998, U.S. provisional patent application Serial No. 60/097,193, filed Aug. 20, 1998, and U.S. provisional patent application Serial No. 60/097,194, filed Aug. 20, 1998, all of which are incorporated herein by reference in their entirety.

STATEMENT REGARDING FEDERALLY SPONSORED RESEARCH OR DEVELOPMENT

Not applicable.

FIELD OF THE INVENTION

The present invention relates to a process for the preparation of hydrocarbons from synthesis gas, (i.e., a mixture of carbon monoxide and hydrogen), typically labeled the Fischer-Tropsch process. Particularly, this invention relates to catalysts containing a xerogel or aerogel matrix, containing cerium oxide, titanium oxide, zirconium oxide or aluminum oxide, for the Fischer-Tropsch process.

BACKGROUND OF THE INVENTION

Large quantities of methane, the main component of natural gas, are available in many areas of the world. Methane can be used as a starting material for the production of hydrocarbons. The conversion of methane to hydrocarbons is typically carried out in two steps. In the first step methane is reformed with water or partially oxidized with oxygen to produce carbon monoxide and hydrogen (i.e., synthesis gas or syngas). In a second step, the syngas is converted to hydrocarbons.

The preparation of hydrocarbons from synthesis gas is well known in the art and is usually referred to as Fischer-Tropsch synthesis, the Fischer-Tropsch process, or Fischer-Tropsch reaction(s). Catalysts for use in such synthesis usually contain a catalytically active Group VIII (CAS) metal. In particular, iron, cobalt, nickel, and ruthenium have been abundantly used as the catalytically active metals. Cobalt and ruthenium have been found to be most suitable for catalyzing a process in which synthesis gas is converted to primarily hydrocarbons having five or more carbon atoms (i.e., where the $C_5^+$ selectivity of the catalyst is high). Additionally, the catalysts often contain one or more promoters and a support or carrier material. Rhenium is a widely used promoter.

The Fischer-Tropsch reaction involves the catalytic hydrogenation of carbon monoxide to produce a variety of products ranging from methane to higher aliphatic alcohols. The methanation reaction was first described in the early 1900's, and the later work by Fischer and Tropsch dealing with higher hydrocarbon synthesis was described in the 1920's.

The Fischer-Tropsch synthesis reactions are highly exothermic and reaction vessels must be designed for adequate heat exchange capacity. Because the feed streams to Fischer-Tropsch reaction vessels are gases while the product streams include liquids, the reaction vessels must have the ability to continuously produce and remove the desired range of liquid hydrocarbon products. The process has been considered for the conversion of carbonaceous feedstock, e.g., coal or natural gas, to higher value liquid fuel or petrochemicals. The first major commercial use of the Fischer-Tropsch process was in Germany during the 1930's. More than 10,000 B/D (barrels per day) of products were manufactured with a cobalt based catalyst in a fixed-bed reactor. This work has been described by Fischer and Pichler in Ger. Pat. No. 731,295 issued Aug. 2, 1936.

Motivated by production of high-grade gasoline from natural gas, research on the possible use of the fluidized bed for Fischer-Tropsch synthesis was conducted in the United States in the mid-1940s. Based on laboratory results, Hydrocarbon Research, Inc. constructed a dense-phase fluidized bed reactor, the Hydrocol unit, at Carthage, Tex., using powdered iron as the catalyst. Due to disappointing levels of conversion, scale-up problems, and rising natural gas prices, operations at this plant were suspended in 1957. Research has continued, however, on developing Fischer-Tropsch reactors such as slurry-bubble columns, as disclosed in U.S Pat. No. 5,348,982 issued Sep. 20, 1994.

Commercial practice of the Fischer-Tropsch process has continued from 1954 to the present day in South Africa in the SASOL plants. These plants use iron-based catalysts, and produce gasoline in relatively high-temperature fluid-bed reactors and wax in relatively low-temperature fixed-bed reactors.

Research is likewise continuing on the development of more efficient Fischer-Tropsch catalyst systems and reaction systems that increase the selectivity for high-value hydrocarbons in the Fischer-Tropsch product stream. In particular, a number of studies describe the behavior of iron, cobalt or ruthenium based catalysts in various reactor types, together with the development of catalyst compositions and preparations.

There are significant differences in the molecular weight distributions of the hydrocarbon products from Fischer-Tropsch reaction systems. Product distribution or product selectivity depends heavily on the type and structure of the catalysts and on the reactor type and operating conditions. Accordingly, it is highly desirable to maximize the selectivity of the Fischer-Tropsch synthesis to the production of high-value liquid hydrocarbons, such as hydrocarbons with five or more carbon atoms per hydrocarbon chain.

U.S. Pat. No. 4,659,681 issued on Apr. 21, 1987, describes the laser synthesis of iron based catalyst particles in the 1–100 micron particle size range for use in a slurry reactor for Fischer-Tropsch synthesis.

U.S. Pat. No. 4,619,910 issued on Oct. 28, 1986, U.S. Pat. No. 4,670,472 issued on Jun. 2, 1987, and U.S. Pat. No. 4,681,867 issued on Jul. 21, 1987, describe a series of catalysts for use in a slurry Fischer-Tropsch process in which synthesis gas is selectively converted to higher hydrocarbons of relatively narrow carbon number range. Reactions of the catalyst with air and water and calcination are specifically avoided in the catalyst preparation procedure. The catalysts are activated in a fixed-bed reactor by reaction with CO+ $H_2$ prior to slurrying in the oil phase in the absence of air.

Catalyst supports for catalysts used in Fischer-Tropsch synthesis of hydrocarbons have typically been oxides (e.g., silica, alumina, titania, zirconia or mixtures thereof, such as silica-alumina). It has been claimed that the Fischer-Tropsch synthesis reaction is only weakly dependent on the chemical identity of the metal oxide support (see E. Iglesia et al. 1993, In: "Computer-Aided Design of Catalysts," ed. E. R. Becker et al., p. 215, New York, Marcel Dekker, Inc.). The products prepared by using these catalysts usually have a very wide range of molecular weights.

U.S. Pat. No. 4,477,595 discloses ruthenium on titania as a hydrocarbon synthesis catalyst for the production of $C_5$ to $C_{40}$ hydrocarbons, with a majority of paraffins in the $C_5$ to $C_{20}$ range. U.S. Pat. No. 4,542,122 discloses a cobalt or cobalt-thoria on titania having a preferred ratio of rutile to anatase, as a hydrocarbon synthesis catalyst. U.S. Pat. No. 4,088,671 discloses a cobalt-ruthenium catalyst where the support can be titania but preferably is alumina for economic reasons. U.S. Pat. No. 4,413,064 discloses an alumina supported catalyst having cobalt, ruthenium and a Group IIIA or Group IVB metal oxide, e.g., thoria. European Patent No. 142,887 discloses a silica supported cobalt catalyst together with zirconium, titanium, ruthenium and/or chromium.

U.S. Pat. No. 4,801,573 discloses a promoted cobalt and rhenium catalyst, preferably supported on alumina that is characterized by low acidity, high surface area, and high purity, which properties are said to be necessary for high activity, jow deactivation, and high molecular weight products. The amount of cobalt is most preferably about 10 to 40 wt % of the catalyst. The content of rhenium is most preferably about 2 to 20 wt % of the cobalt content. Related U.S. Pat. No. 4,857,559 discloses a catalyst most preferably having 10 to 45 wt % cobalt and a rhenium content of about 2 to 20 wt % of the cobalt content. In both of the above patents the method of depositing the active metals and promoter on the alumina support is described as not critical.

U.S. Pat. No. 5,545,674 discloses a cobalt-based catalyst wherein the active metal is dispersed as a very thin film on the surface of a particulate support, preferably silica or titania or a titania-containing support. The catalyst may be prepared by spray techniques.

U.S. Pat. No. 5,028,634 discloses supported cobalt-based catalysts, preferably supported on high surface area aluminas. High surface area supports are said to be preferred because greater cobalt dispersion can be achieved as cobalt is added, with less tendency for one crystal of cobalt to fall on another crystal of cobalt. The cobalt loading on a titania support is preferably 10 to 25 wt %, while the preferred cobalt loading on an alumina support is 5 to 45 wt %.

International Publication Nos. WO 98/47618 and WO 98/47620 disclose the use of rhenium promoters and describe several functions served by the rhenium.

U.S Pat. No. 5,248,701 discloses a copper promoted cobalt-manganese spinel that is said to be useful as a Fischer-Tropsch catalyst with selectivity for olefins and higher paraffins.

U.S. Pat. No. 5,302,622 discloses a supported cobalt and ruthenium based catalyst including other components and preferably prepared by a gelling procedure to incorporate the catalyst components in an alcogel formed from a hydrolyzable compound of silicon, and/or aluminum, and optional compounds. The cobalt content after calcination is preferably between 14 and 40 wt % of the catalyst.

UK Patent Application GB 2,258,414A, published Feb. 10, 1993, discloses a supported catalyst containing cobalt, molybdenum and/or tungsten, and an additional element. The support is preferably one or more oxides of the elements Si, Al, Ti, Zr, Sn, Zn, Mg, and elements with atomic numbers from 57 to 71. After calcination, the preferred cobalt content is from 5 to 40 wt % of the catalyst. A preferred method of preparation of the catalyst includes the preparation of a gel containing the cobalt and other elements.

International Publication No. WO 96/19289 discloses active metal coated catalysts supported on an inorganic oxide, and notes that dispersion of the active metal on Fischer-Tropsch catalysts has essential effects on the activity of the catalyst and on the composition of the hydrocarbons obtained.

Despite the vast amount of research effort in this field, there is still a great need for new catalysts for Fischer-Tropsch synthesis, particularly catalysts that provide high $C_5^+$ hydrocarbon selectivities to maximize the value of the hydrocarbons produced and thus enhance the process economics.

SUMMARY OF THE INVENTION

This invention provides a process and catalyst for producing hydrocarbons, and a method for preparing the catalyst. The process comprises contacting a feed stream comprising hydrogen and carbon monoxide with a catalyst in a reaction zone maintained at conversion-promoting conditions effective to produce an effluent stream comprising hydrocarbons wherein the catalyst comprises a catalytically active metal selected from the group consisting of iron, cobalt, nickel, ruthenium, and combinations thereof dispersed in a matrix material comprising a derivative of a destabilized aquasol comprising a colloidal oxide of a matrix metal selected from the group consisting of cerium, zirconium, titanium, aluminum, silicon, and combinations thereof.

In accordance with this invention, another catalyst used in the process comprises a reduced aerogel or xerogel formed from the destabilization of a colloidal mixture comprising a catalytically active metal selected from the group consisting of iron, cobalt, nickel, ruthenium, aluminum, and combinations thereof and a colloidal sol of a matrix metal selected from the group consisting of cerium, zirconium, titanium, aluminum, silicon, and combinations thereof.

This invention also includes a method for the preparation of a Fischer-Tropsch catalyst comprising mixing a colloidal sol of an oxide of a metal selected from the group consisting of cerium, zirconium, titanium, aluminum, silicon, and combinations thereof with a soluble salt of one or more catalytically active metals selected from the group consisting of iron, cobalt, nickel, and ruthenium, destabilizing the colloid to form a gel, and removing solvent from the gel.

This invention also provides a process for producing hydrocarbons by contacting a feed stream comprising hydrogen and carbon monoxide with a catalyst in a reaction zone maintained at conversion-promoting conditions effective to produce an effluent stream comprising the hydrocarbons. The process of this invention is characterized by using a catalyst prepared by a method comprising (1) forming a catalyst gel by destabilizing an aqueous colloid comprising (a) at least one catalytic metal for Fischer-Tropsch reactions (e.g., at least one metal selected from the group consisting of iron, cobalt, nickel and ruthenium), (b) at least one colloidal oxide selected from the group consisting of cerium oxide, zirconium oxide, titanium oxide and aluminum oxide, and optionally (c) at least one alkoxide selected from the group consisting of $Al(OR)_3$, $Si(OR)_4$, $Ti(OR)_4$ and $Zr(OR)_4$, where each R is an alkyl group having from 1 to 6 carbon atoms; and (2) drying the gel.

DETAILED DESCRIPTION OF THE INVENTION

The feed gases charged to the process of the invention comprise hydrogen, or a hydrogen source, and carbon monoxide. $H_2/CO$ mixtures suitable as a feedstock for conversion to hydrocarbons according to the process of this invention can be obtained from light hydrocarbons such as methane by means of steam reforming, partial oxidation, or other processes known in the art. The hydrogen is preferably provided by free hydrogen, although some Fischer-Tropsch catalysts have sufficient water gas shift activity to convert some water to hydrogen for use in the Fischer-Tropsch process. It is preferred that the molar ratio of hydrogen to carbon monoxide in the feed be greater than 0.5:1 (e.g., from about 0.67 to 2.5). When cobalt, nickel, and/or ruthenium catalysts are used, the feed gas stream preferably contains hydrogen and carbon monoxide in a molar ratio of about 2:1. When iron catalysts are used, the feed gas stream preferably contains hydrogen and carbon monoxide in a molar ratio of about 0.67:1. The feed gas may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds, such as hydrogen sulfide, ammonia and carbonyl sulfides.

The feed gas is contacted with the catalyst in a reaction zone. Mechanical arrangements of conventional design may be employed as the reaction zone including, for example, fixed bed, fluidized bed, slurry phase, slurry bubble column or ebullating bed reactors, among others, may be used. Accordingly, the size and physical form of the catalyst particles may vary depending on the reactor in which they are to be used.

Catalyst Preparation

A component of the catalysts used in this invention is the matrix material, which is essentially derived from at least one colloidal oxide and optionally at least one metal alkoxide, and which incorporates at least one catalytic metal for Fischer-Tropsch reactions.

A matrix is a skeletal framework of oxides and oxyhydroxides which in the present invention is derived from the colloids used. The framework typically comprises 35% or more, by weight, of the total catalyst composition. Preferably, the matrix material (i.e., cerium oxide, zirconium oxide, titanium oxide and/or aluminum oxide and optionally silicon oxide) totals from 99.9 to 35 mole %, preferably from 50 to 85 mole % of the catalyst composition. More preferable are combinations where the matrix is cerium oxide, titanium oxide or a mixture of titanium and aluminum oxides (e.g., a mixture wherein the Ti:Al atomic ratio is between about 5:95 and 95:1).

A gel may be described as a coherent, rigid three-dimensional polymeric network. The present gels are formed in a liquid medium, usually water, alcohol, or a mixture thereof. The term "alcogel" describes gels in which the pores are filled with predominantly alcohol. Gels whose pores are filled primarily with water may be referred to as aquagels or hydrogels.

A "xerogel" is a gel from which the liquid medium has been removed and replaced by a gas. In general, the structure is compressed and the porosity reduced significantly by the surface tension forces that occur as the liquid is removed. As soon as liquid begins to evaporate from a gel at temperatures below the critical temperature, surface tension creates concave menisci in the gel's pores. As evaporation continues, the menisci retreat into the gel body, compressive forces build up around its perimeter, and the perimeter contracts, drawing the gel body inward. Eventually, surface tension causes significant collapse of the gel body and a reduction of volume, often as much as two-thirds or more of the original volume. This shrinkage causes a significant reduction in the porosity, often as much as 90 to 95 percent depending on the system and pore sizes.

In contrast, an "aerogel" is a gel from which the liquid has been removed in such a way as to prevent significant collapse or change in the structure as liquid is removed. This is typically accomplished by heating the liquid-filled gel in an autoclave while maintaining the prevailing pressure above the vapor pressure of the liquid until the critical temperature of the liquid has been exceeded, and then gradually releasing the vapor, usually by gradually reducing the pressure either incrementally or continuously, while maintaining the temperature above the critical temperature. The critical temperature is the temperature above which it is impossible to liquefy a gas, regardless of how much pressure is applied. At temperatures above the critical temperature, the distinction between liquid and gas phases disappears and so do the physical manifestations of the gas/liquid interface. In the absence of an interface between liquid and gas phases, there is no surface tension and hence no surface tension forces to collapse the gel. Such a process may be termed "super critical drying." Aerogels produced by super critical drying typically have high porosities, on the order of from 50 to 99 percent by volume.

In the practice of this invention one or more inorganic metal colloids may be used as starting material for preparing the gels. These colloids include colloidal alumina sols, colloidal ceria sols, colloidal zirconia sols or their mixtures. The colloidal sols are commercially available. There are also several methods of preparing colloids, as described in "Inorganic Colloid Chemistry", Volumes 1, 2 and 3, J. Wiley and Sons, Inc., 1935. Colloid formation involves either nucleation and growth, or subdivision or dispersion processes. For example, hydrous titanium dioxide sols can be prepared by adding ammonia hydroxide to a solution of a tetravalent titanium salt, followed by peptization (re-dispersion) by dilute alkalis. Zirconium oxide sol can be prepared by dialysis of sodium oxychlorides. Cerium oxide sol can be prepared by dialysis of a solution of ceric ammonium nitrate.

Commercially available alkoxides, such as tetraethylorthosilicate and Tyzor™ organic titanate esters, can be used. However, inorganic alkoxides can be prepared by various routes. Examples include direct reaction of zero valent metal with alcohols in the presence of a suitable catalyst; and the reaction of metal halides with alcohols. Alkoxy derivatives can be synthesized by the reaction of the alkoxide with alcohol in a ligand interchange reaction. Direct reactions of metal dialkamides with alcohol also form alkoxide derivatives. Additional examples are disclosed in D. C. Bradley et al., "Metal Alkoxides" (Academic Press, 1978).

In a preferred embodiment of the process of this invention, pre-formed colloidal sols in water, or aquasols, are used. The aquasols are comprised of colloidal particles ranging in size from 2 to 50 nanometers. In general, the smaller primary particle sizes (2 to 5 nm) are preferred. The pre-formed colloids contain from 10 to 35 weight % of colloidal oxides or other materials, depending on the method of stabilization. Generally, after addition of the active (for Fischer-Tropsch reactions, either as a catalyst or promoter) metal components, the final de-stabilized colloids can possess from about 1 to 35 weight % solids, preferably from about 1 to 20 weight %.

The colloidal oxides or their mixtures are destabilized during the addition of soluble salts of the primary and promoter cation species by the addition of acids or bases or by solvent removal, both of which alter pH. These changes modify the colloidal particle's electrical double layer. Each colloidal particle possesses a double layer when suspended in a liquid medium. For instance, a negatively charged colloid causes some of the positive ions to form a firmly attached layer around the surface of a colloid. Additional positive ions are still attracted by the negative colloid, but now they are repelled by the primary positive layer as well as the positive ions, and form a diffuse layer of counterions. The primary layer and the diffuse layer are referred to as the double layer. The tendencies of a colloid to either agglomerate (flocculate and precipitate) or polymerize when destabilized will depend on the properties of this double layer. The double layer, and resulting electrostatic forces can be modified by altering the ionic environment, or pH, liquid concentration, or by adding a surface active material directly to affect the charge of the colloid.

Once the particles come in close enough contact when destabilized, polymerization and crosslinking reaction between surface functional groups, such as surface hydroxyls, can occur. In this invention, the colloids, which are originally stable heterogeneous dispersions of oxides and other species in solvents, are destabilized to produce colloidal gels. Destabilization is induced, in some cases, by the addition of soluble salts, e.g., chlorides or nitrates, which change the pH and the ionic strength of the colloidal suspensions; by the addition of acids or bases; or by solvent removal. pH changes generally accompany the addition of soluble salts; in general, this is preferred over solvent removal. Generally, a pH range of from about 0 to about 12 can be used to destabilize the colloids; however, very large extremes in pH (such as pH 12) can cause flocculation and precipitation. For this reason, a pH range of from about 2 to 8 is generally preferred.

The medium utilized in this process is typically aqueous, although non-aqueous colloids can also be used. The additional metal or inorganic reagents (e.g., salts of Ru, Co, or promoters) used should be soluble in the appropriate aqueous and non-aqueous media.

Removal of solvent from the gels can be accomplished by several methods. Removal by vacuum drying or heating in air results in the formation of a xerogel. An aerogel of the material can typically be formed by charging in a pressurized system such as an autoclave. In some cases, water solvent (which may be present in the gels formed) may need to be exchanged with a non-aqueous solvent prior to supercritical pressure extraction. The solvent-containing gel which is formed in the practice of the invention is placed in an autoclave, where it can be contacted with a fluid above its critical temperature and pressure by allowing the supercritical fluid to flow through the gel material until the solvent is no longer being extracted by the supercritical fluid. In performing this extraction to produce an aerogel material, various fluids can be utilized at their critical temperature and pressure. For instance, fluorochlorocarbons typified by Freon® fluorochloromethanes (e.g., Freon® 11 ($CCl_3F$), 12 ($CCl_2F_2$) or 114 ($CClF_2CClF_2$), ammonia and carbon dioxide are all suitable for this process. Typically, the extraction fluids are gases at atmospheric conditions, so that pore collapse due to the capillary forces at the liquid/solid interface is avoided during drying. The material dried under supercritical conditions will, in most cases, possess a higher surface area than the materials dried by other means.

Catalytically Active Metals

Another component of the catalyst of the present invention is the catalytic metal. The catalytic metal is preferably selected from iron, cobalt, nickel and/or ruthenium. Normally, the metal component on the support or matrix is reduced to provide elemental metal (e.g., elemental iron, cobalt, nickel and/or ruthenium) before use. The catalyst must contain a catalytically effective amount of the metal component(s). Typically, the catalyst comprises from about 0.1 to 50 mole % (as the metal) of total supported iron, cobalt, nickel and/or ruthenium per total moles of catalytic metal and matrix metal (i.e., Ce, Zr, Ti, Al and Si), preferably from about 5 to 50 mole %.

Each of the catalytic metals can be used individually or in combination, especially cobalt and ruthenium. In one preferred embodiment, catalysts of this invention comprise from about 10 to 50 mole percent of a combination of cobalt and ruthenium where the ruthenium content is from about 0.001 to about 5 mole percent. Also preferred are embodiments where these combinations are combined with a matrix of titanium oxide, cerium oxide, aluminum oxide, a mixture of cerium and aluminum oxides, or a mixture of titanium and aluminum oxides.

In another preferred embodiment, the catalysts of the present invention may comprise one or more additional promoters or modifiers known to those skilled in the art. When the catalytic metal is iron, cobalt, nickel and/or ruthenium, suitable promoters include at least one metal selected from the group consisting of Group IA (CAS) metals (i.e., Na, K, Rb, Cs), Group IIA metals (i.e., Mg, Ca, Sr, Ba), Group IB metals (i.e., Cu, Ag, and Au) Group IIIB metals (i.e., Sc, Y and La), Group IVB metals (i.e., Ti, Zr and Hf), Group VB metals (i.e., V, Nb and Ta), and Rh, Pd, Os, Ir, Pt, Mn, B, P, and Re. Preferably, any additional promoters for the cobalt and/or ruthenium are selected from Sc, Y, La, Ti, Zr, Hf, Rh, Pd, Os, Ir, Pt, Re, Nb, Cu, Ag, Mn, B, P, and Ta. Preferably, any additional promoters for the iron catalysts are selected from Na, K, Rb, Cs, Mg, Ca, Sr and Ba.

The amount of additional promoter, if present, is typically between 0.001 and 20 mole %, preferably from 2 to 5 mole %. More preferably, the catalysts comprise from about 5 to about 50 mole percent of a combination of cobalt and rhenium where the rhenium content is from about 0.001 to about 5 mole percent; and catalysts comprising from about 5 to about 50 mole percent a combination of cobalt and both rhenium and ruthenium where the rhenium and ruthenium together total from about 0.001 to about 5 mole percent. Preferably, these combinations are combined with a matrix of titanium oxide, cerium oxide, aluminum oxide, a mixture of cerium and aluminum oxides, a mixture of titanium and aluminum oxides, or a mixture of silicon and aluminum oxides.

The most preferred method of preparation may vary among those skilled in the art, depending for example on the desired catalyst particle size. Those skilled in the art are able to select the most suitable method for a given set of requirements.

Process and Conditions

Typically, at least a portion of the metal(s) of the catalytic metal component (a) of the catalysts of the present invention is present in a reduced state (i.e., in the metallic state). Therefore, it is normally advantageous to activate the catalyst prior to use by a reduction treatment, in the presence of hydrogen at an elevated temperature. Typically, the catalyst is treated with hydrogen at a temperature in the range of from about 75° C. to about 500° C., for about 0.5 to about 24 hours at a pressure of about 1 to about 75 atm. Pure hydrogen may be used in the reduction treatment, as well as a mixture of hydrogen and an inert gas such as nitrogen. The amount of hydrogen may range from about 1% to about 100% by volume.

The Fischer-Tropsch process is typically run in a continuous mode. In this mode, the gas hourly space velocity through the reaction zone typically may range from about 100 volumes/hour/volume catalyst (v/hr/v) to about 10,000 v/hr/v, preferably from about 300 v/hr/v to about 2,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psig (653 kPa) to about 1000 psig (6994 kPa), preferably, from 80 psig (653 kPa) to about 600 psig (4237 kPa), and still more preferably, from about 140 psig (1066 kPa) to about 400 psig (2858 kPa).

The products resulting from the process will have a great range of molecular weights. Typically, the carbon number range of the product hydrocarbons will start at methane and continue to the limits observable by modem analysis, about 50 to 100 carbons per molecule. The process is particularly useful for making hydrocarbons having five or more carbon atoms, especially when the above-referenced preferred space velocity, temperature and pressure ranges are employed.

The wide range of hydrocarbons produced in the reaction zone will typically afford liquid phase products at the reaction zone operating conditions. Therefore, the effluent stream of the reaction zone will often be a mixed phase stream including liquid and vapor phase products. The effluent stream of the reaction zone may be cooled to effect the condensation of additional amounts of hydrocarbons and passed into a vapor-liquid separation zone separating the liquid and vapor phase products. The vapor phase material may be passed into a second stage of cooling for recovery of additional hydrocarbons. The liquid phase material from the initial vapor-liquid separation zone, together with any liquid from a subsequent separation zone, may be fed into a fractionation column. Typically, a stripping column is employed first to remove light hydrocarbons such as propane and butane. The remaining hydrocarbons may be passed into a fractionation column where they are separated by boiling point range into products such as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reactor zone effluent stream after hydrocarbon recovery may be partially recycled if it contains a sufficient quantity of hydrogen and/or carbon monoxide.

Without further elaboration, it is believed that one skilled in the art can, using the description herein, utilize the present invention to its fullest extent. The following embodiments are to be construed as illustrative, and not as constraining the scope of the present invention in any way whatsoever.

EXAMPLES

General Procedure for Batch Tests

Each of the catalyst samples was treated with hydrogen prior to use in the Fischer-Tropsch reaction. The catalyst sample was placed in a small quartz crucible in a chamber and purged with 500 sccm ($8.3 \times 10^{-6}$ m$^3$/s) nitrogen at room temperature for 15 minutes. The sample was then heated under 100 sccm ($1.7 \times 10^{-6}$ m$^3$/s) hydrogen at 1° C./minute to 100° C. and held at 100° C. for one hour. The catalysts were then heated at 1° C./minute to 400° C. and held at 400° C. for four hours under 100 sc/cm ($1.7 \times 10^{-6}$ hydrogen. The samples were cooled in hydrogen and purged with nitrogen before use.

A 2 mL pressure vessel was heated at either 225° C. under 1000 psig (6994 kPa) of H$_2$:CO (2:1) and maintained at that temperature and pressure for 1 hour. In a typical run, roughly 50 mg of the hydrogen catalyst and 1 mL of n-octane was added to the vessel. After one hour, the reactor vessel was cooled in ice, vented, and an internal standard of di-n-butylether was added. The reaction product was analyzed on an HP6890 gas chromatograph. Hydrocarbons in the range of $C_{11}$–$C_{40}$ were analyzed relative to the internal standard. The lower hydrocarbons were not analyzed since they are masked by the solvent and are also vented as the pressure is reduced.

A $C_{11}^+$ Productivity (g $C_{11}^+$/hour/kg catalyst) was calculated based on the integrated production of the $C_{11}$–$C_{40}$ hydrocarbons per kg of catalyst per hour. The logarithm of the weight fraction for each carbon number 1 n($W_n$/n) was plotted as the ordinate vs. number of carbon atoms in ($W_n$/n) as the abscissa. From the slope, a value of alpha was obtained. Some runs displayed a double alpha as shown in the tables. The results of runs over a variety of catalysts at 225° C. are shown in Table 1.

Catalyst Preparation

The catalyst compositions are given in atomic ratios except where otherwise noted.

EXAMPLE 1

To a 150 mL petri dish, ruthenium (III) chloride (17.525 mL of a 0.1151 M aqueous solution), cobalt (II) chloride (18.154 mL of a 1.0 M aqueous solution) and colloidal alumina sol (4.321 mL, 4.668 M or 20 wt. %) were simultaneously combined. The pH of the alumina sol was 4.0. The pH of the resultant mixture, after addition of the reagents, was approximately 1.37. At that point the colloid was destabilized to form a dark gel-like material. The material was aged for five days before drying under vacuum at 150° C. for 5 hours.

The final xerogel had a nominal composition of Ru (0.05)/Co (0.45)/Al (0.5).

EXAMPLE 2

To a 150 mL petri dish, ruthenium (III) chloride (17.357 mL of a 0.1151 M aqueous solution), cobalt (II) chloride hexahydrate (CoCl$_2$.6H$_2$O, 17.960 mL of a 1.0 M aqueous solution) and colloidal alumina sol (4.280 mL, 4.668 M or 20 wt. %) were simultaneously combined. In a second step, 0.404 mL of a 1.0 M cesium chloride solution was added. The colloid was destabilized to form a dark red gel-like material. The material was aged for five days before drying under vacuum at 150° C. for 5 hours.

The final xerogel had a nominal composition Ru (0.0495)/Co (0.445)/Cs (0.01)/Al (0.495).

EXAMPLE 3

To a 150 mL petri dish, ruthenium (III) chloride (16.641 mL of a 0.1151 M aqueous solution), cobalt (II) chloride hexahydrate (CoCl$_2$.6H$_2$O, 17.239 mL of a 1.0 M aqueous solution) and colloidal alumina sol (4.103 mL, 4.668 M or 20 wt. %) were simultaneously combined. In a second step, 2.016 mL of a 1 M aqueous lithium nitrate (LiNO$_3$) solution were added. The colloid was destabilized to form a dark red gel-like material. The material was aged for five days before drying under vacuum at 150° C. for 5 hours.

The final xerogel had a nominal composition of Ru (0.0475)/Co (0.4275)/Li(0.05)/Al (0.475).

EXAMPLE 4

To a 150 mL petri dish, ruthenium (III) chloride (16.641 mL of a 0.1151 M aqueous solution), cobalt (II) chloride hexahydrate ($CoCl_2 \cdot 6H_2O$, 17.239 mL of a 1.0 M aqueous solution) and colloidal alumina sol (4.103 mL, 4.668 M or 20 wt. %) were simultaneously combined. In a second step, 2.016 mL of a 1 M aqueous solution of rubidium nitrate were added. The colloid was destabilized to form a dark red gel-like material. The material was aged for five days before drying under vacuum at 150° C. for 5 hours.

The final xerogel had a nominal composition of Ru (0.0475)/Co (0.4275)/Rb(0.05)/Al (0.475).

EXAMPLE 5

To a 150 mL petri dish, ruthenium (III) chloride (17.072 mL of a 0.1151 M aqueous solution), cobalt (II) chloride hexahydrate ($CoCl_2 \cdot 6H_2O$, 17.685 mL of a 1.0 M aqueous solution) and colloidal alumina sol (4.209 mL, 4.668 M or 20 wt. %) were simultaneously combined. In a second step, 1.034 mL of a 2.0 M aqueous sodium chloride solution were added. The colloid was destabilized to form a dark red gel-like material. The material was aged for five days before drying under vacuum at 150° C. for 5 hours.

The final xerogel had a nominal composition Ru (0.0475)/Co (0.4275)/Na(0.05)/Al (0.475).

EXAMPLE 6

To a 150 mL petri dish, ruthenium (III) chloride (17.072 mL of a 0.1151 M aqueous solution), cobalt (II) chloride hexahydrate ($CoCl_2 \cdot 6H_2O$, 17.685 mL of a 1.0 M aqueous solution) and colloidal alumina sol (4.209 mL, 4.668 M or 20 wt. %) were simultaneously combined. In a second step, 1.034 mL of 2.0 M aqueous potassium chloride (KCl) solution were added. The colloid was destabilized to form a red gel-like material. The material was aged for five days before drying under vacuum at 150° C. for 5 hours.

The final xerogel had a nominal composition of Ru (0.0475)/Co (0.4275)/K(0.05)/Al (0.475).

EXAMPLE 7

To a 150 mL petri dish, ruthenium (III) chloride (16.641 mL of a 0.1151 M aqueous solution), cobalt (II) chloride hexahydrate ($CoCl_2 \cdot 6H_2O$, 17.239 mL of a 1.0 M aqueous solution) and colloidal alumina sol (4.103 mL, 4.668 M or 20 wt. %) were simultaneously combined. In a second step, 2.016 mL of 1.0 M aqueous cesium chloride solution were added. The colloid was destabilized to form a red gel-like material. The material was aged for five days be fore drying under vacuum at 150° C. for 5 hours.

The final xerogel had a nominal composition of Ru (0.0475)/Co (0.4275)/K(0.05)/Al (0.475).

EXAMPLE 8

An aqueous solution of ruthenium (III) chloride (4.951 mL, 0.1151 M), an aqueous solution of cobalt (II) chloride (22.793 mL, 1 M), tetraethylorthosilicate (11.248 mL) and 0.72 mL of colloidal alumina sol (20 wt. %) were combined in a 150 mL petri dish under an inert atmosphere. In a second step, aqueous HCl (0.288 mL, 1.0 M) was added with swirling. The final pH of the mixture was 1.51. A red homogeneous, clear gel formed after several hours. The material was aged for four days, and dried under vacuum at 120° C. for 5 hours.

The final xerogel had a nominal composition of Ru (0.01)/Co (0.4)/Al (0.059)/Si(0.53 1).

EXAMPLE 9

An aqueous solution of ruthenium (III) chloride (5.202 mL, 0.1151 M), an aqueous solution of cobalt (II) chloride (23.950 mL, 1 M), tetraethylorthosilicate (60 volume % solution in absolute ethanol, 1.313 mL) and 6.811 mL of colloidal alumina sol (4.668 M or 20 wt. %) were combined in a 150 mL petri dish under an inert atmosphere. In a second step, aqueous HCl (2.724 mL, 1.0 M) was added with swirling. The final pH of the mixture was 1.00. A red-brown homogeneous, clear gel formed after the addition of the reagents, which destabilize the gel. The material was aged for four days, and dried under vacuum at 120° C. for 5 hours.

The final xerogel had a nominal composition of Ru (0.01)/Co (0.4)/Al (0.531)/Si (0.059).

EXAMPLE 10

An aqueous solution of ruthenium (III) chloride (5.062 mL, 0.1151 M), an aqueous solution of cobalt (II) chloride (23.306 mL, 1 M), and 6.628 mL of colloidal alumina sol (4.668 M or 20 wt. %) were combined in a 150 mL petri dish under an inert atmosphere. In a second step, aqueous HCl (3.323 mL, 1.0 M) and 1.681 mL of 2.045 M colloidal zirconium oxide (acetate stabilized) were added with swirling. The final. pH of the mixture was 1.55. A dark red-brown homogeneous gel formed when destabilized by the addition of the reagents. The material was aged for four days, and dried under vacuum at 120° C. for 5 hours.

The final xerogel had a nominal composition Ru (0.01)/Co (0.4)/Zr(0.059)/Al (0.531).

EXAMPLE 11

An aqueous solution of ruthenium (III) chloride (18.780 mL, 0.1151 M), 12.960 mL of colloidal cerium oxide (1.4177 M), 3.936 mL of colloidal alumina sol (4.668 M or 20 wt. %), and 4.323 mL of 1 M aqueous $CoCl_2 \cdot 6H_2O$ were combined in a 150 mL petri dish under an inert atmosphere. The final pH of the mixture was 1.32. A gel-like material formed. The material was aged for four days, and dried under vacuum at 120° C. for 5 hours.

The final xerogel had a nominal composition Ru (0.05)/Co (0.1)/Ce (0.425)/Al (0.425).

EXAMPLE 12

An aqueous solution of ruthenium (III) chloride (18.780 mL, 0.1151 M), 23.960 mL of colloidal cerium oxide (1.4177 M), and 3.936 mL of colloidal alumina sol (4.668 M or 20 wt. %) were combined in a 150 mL petri dish under an inert atmosphere. In a second step, 4.323 mL of 1.0 M aqueous nickel chloride hexahydrate ($NiCl_2 \cdot 6H_2O$) was added with swirling. The final pH of the mixture was 1.32. A red-brown homogeneous, clear gel formed. The material was aged for four days, and dried under vacuum at 120° C. for 5 hours.

The final xerogel had a nominal composition of Ru (0.05)/Ni (0.1)/Ce (0.425)/Al (0.425).

EXAMPLE 13

An aqueous solution of ruthenium (III) chloride (3.00 mL, 0.1151 M), 20.701 mL of colloidal cerium oxide (1.4177 M), 6.287 mL of colloidal alumina sol (4.668 M or 20 wt. %), and 10.013 mL of 1.0 M aqueous cobalt chloride hexahydrate solution ($CoCl_2 \cdot 6H_2O$) were combined in a 150 mL petri dish under an inert atmosphere. The final pH of the mixture was 1.97. A dark gel-like material formed. The material was aged for four days, and dried under vacuum at 120° C. for 5 hours.

The final xerogel had a nominal composition of Ru (0.005)/Co (0.145)/Ce (0.425)/Al (0.425).

EXAMPLE 14

An aqueous solution of ruthenium (III) chloride (18.78 mL, 0.1151 M), 12.960 mL of colloidal cerium oxide (1.4177 M), 3.936 mL of colloidal alumina sol (4.668 M or 20 wt. %), and 2.162 mL of 1.0 M aqueous cobalt chloride hexahydrate solution ($CoCl_2.6H_2O$) were combined in a 150 mL petri dish under an inert atmosphere. In a second step, 2.162 mL of 1 M aqueous nickel chloride solution ($NiCl_2.6H_2O$) were added. The final pH of the mixture was 1.34. A gel-like material formed. The material was aged for four days, and dried under vacuum at 120° C. for 5 hours.

The final xerogel had a nominal composition of Ru (0.05)/Co (0.050/Ni (0.05)/Ce (0.425)/Al (0.425).

EXAMPLE 15

An aqueous solution of ruthenium (III) chloride (15.5394 mL, 0.1151 M), 6.330 mL of colloidal cerium oxide (1.4177 M) and 1.922 mL of colloidal alumina sol (4.668 M or 20 wt. %) were combined in a 150 mL petri dish under an inert atmosphere. In a second step, 16.154 mL of a 1 M aqueous nickel chloride solution ($NiCl_2.6H_2O$) were added. The final pH of the mixture was 1.34. A gel-like material formed. The material was aged for four days, and dried under vacuum at 120° C. for 5 hours.

The final xerogel had a nominal composition of Ru (0.05)/Ni (0.45)/Ce (0.25)/Al (0.25).

EXAMPLE 16

An aqueous solution of ruthenium (III) chloride (14.046 mL, 0.1151 M), 11.404 mL of colloidal cerium oxide (1.4177 M) and 14.550 mL of 1.0 M aqueous cobalt chloride hexahydrate solution ($CoCl_2.6H_2O$) were combined in a 150 mL petri dish under an inert atmosphere. The final pH of the mixture was 1.51. A gel-like material formed. The material was aged for four days, and dried under vacuum at 120° C. for 5 hours.

The final xerogel had a nominal composition of Ru (0.05)/Co (0.45)/Ce (0.5).

TABLE 1

| | (225° C.) | | |
|---|---|---|---|
| Ex. No. | Catalyst | $C_{11}^+$ Productivity | Alpha |
| 1 | Ru (0.05)/Co (0.45)/Al (0.5) | 368 | 0.88 |
| 2 | Ru (0.0495)/Co (0.445)/Cs (0.01)/Al (0.495) | 153 | 0.8 |
| 3 | Ru (0.0475)/Co (0.4275)/Li (0.05)/Al (0.475) | 208 | 0.78 |
| 4 | Ru (0.0475)/Co (0.4275)/Rb (0.05)/Al (0.475) | 260 | 0.8 |
| 5 | Ru (0.0475)/Co (0.4275)/Na (0.05)/Al (0.475) | 256 | 0.77 |
| 6 | Ru (0.0475)/Co (0.4275)/K (0.05)/Al (0.475) | 166 | 0.76 |
| 7 | Ru (0.0475)/Co (0.4275)/Cs (0.05)/Al (0.475) | 159 | 0.81 |
| 8 | Ru (0.01)/Co (0.4)/Al (0.059)/Si (0.531) | 110 | 0.78/0.92 |
| 9 | Ru (0.01)/Co (0.4)/Al (0.531)/Si (0.059) | 88 | 0.79/0.89 |
| 10 | Ru (0.01)/Co (0.4)/Zr (0.059)/Al (0.531) | 69 | 0.77/0.89 |
| 11 | Ru (0.05)/Ce (0.425)/Al (0.425) | 53 | 0.78/0.9 |
| 12 | Ru (0.05)/Ni (0.1)/Ce (0.425)/Al (0.425) | 6 | 0.76/0.9 |

TABLE 1-continued

| | (225° C.) | | |
|---|---|---|---|
| Ex. No. | Catalyst | $C_{11}^+$ Productivity | Alpha |
| 13 | Ru (0.005)/Co (0.145)/Ce (0.425)/Al (0.425) | 11 | 0.81 |
| 14 | Ru (0.05)/Co (0.050/Ni (0.05)/Ce (0.425)/Al (0.425) | 13 | 0.83 |
| 15 | Ru (0.05)/Ni (0.45)/Ce (0.25)/Al (0.25) | 11 | 0.77 |
| 16 | Ru (0.05)/Co (0.45)/Ce (0.5) | 115 | 0.81 |

While a preferred embodiment of the present invention has been shown and described, it will be understood that variations can be made to the preferred embodiment without departing from the scope of, and which are equivalent to, the present invention. For example, the structure and composition of the catalyst can be modified and the process steps can be varied.

The complete disclosures of all patents, patent documents, and publications cited herein are incorporated by reference in their entirety. U.S patent application Ser. No. 09/377,007 entitled Fischer-Tropsch Processes Using Xerogel and Aerogel Catalysts, and U.S patent application Ser. No. 09/376,873, entitled Fischer-Tropsch Processes Using Catalysts on Mesoporous Supports, both filed concurrently herewith on Aug. 18, 1999, are hereby incorporated herein by reference in their entirety.

U.S. patent application Ser. No. 09/314,921, entitled Fischer-Tropsch Processes and Catalysts using Fluorided Supports, filed May 19, 1999, U.S. patent application No. 09/314,920, entitled Fischer-Tropsch Processes and Catalysts Using Fluorided Alumina Supports, filed May 19, 1999, and U.S. patent application Ser. No. 09/314,811, entitled Fischer-Tropsch Processes and Catalysts With Promoters, filed May 19, 1999, are hereby incorporated herein by reference in their entirety.

The foregoing detailed description and examples have been given for clarity of understanding only. No unnecessary limitations are to be understood therefrom. The invention is not limited to the exact details shown and described, for variations obvious to one skilled in the art will be included within the invention by the claims.

What is claimed is:

1. A process for producing hydrocarbons, comprising contacting a feed stream comprising hydrogen and carbon monoxide with a catalyst in a reaction zone maintained at conversion-promoting conditions effective to produce an effluent stream comprising hydrocarbons, wherein the catalyst comprises a catalytically active metal selected from the group consisting of iron, cobalt, nickel, ruthenium, and combinations thereof dispersed in a matrix material comprising a derivative of a destabilized aquasol comprising a colloidal oxide of a matrix metal selected from the group consisting of cerium, zirconium, titanium, aluminum, silicon, and combinations thereof.

2. The process of claim 1 wherein the matrix material content of the catalyst is from about 99.9 to about 35 mole percent.

3. The process of claim 2 wherein the matrix material content of the catalyst is from about 50 to 85 mole percent.

4. The process of claim 2 wherein the matrix metal is selected from the group consisting of cerium, titanium, aluminum, and combinations thereof.

5. The process of claim 4 wherein the matrix metal is a combinations of titanium and aluminum, and the atomic ratio of titanium to aluminum is from about 5:95 to about 95:1.

6. The process of claim 1 wherein the catalytically active metal comprises from about 0.1 to 50 mole percent of the matrix metal and catalyst metal combined.

7. The process of claim 6 wherein the catalytically active metal comprises from about 10 to 50 mole percent of the matrix metal and catalyst metal combined.

8. The process of claim 7 wherein the catalytically active metal comprises cobalt and ruthenium and wherein the content of the catalytically active metal comprises from about 5 to 50 mole percent of the matrix metal and catalyst metal combined.

9. The process of claim 8 wherein the ruthenium content is from about 0.001 to about 5 mole percent of the matrix metal and catalyst metal combined.

10. The process of claim 9 wherein the matrix metal is selected from the group consisting of titanium, cerium, aluminum, a mixture of cerium and aluminum, a mixture of silicon and aluminum, and a mixture of titanium and aluminum.

11. The process of claim 1 wherein the catalyst comprises one or more promoters selected from the group consisting of Na, K, Rb, Cs, Mg, Ca, Sr, Ba, Cu, Ag, Au, Sc, Y, La, Ti, Zr, Hf, V, Nb, Ta, Rh, Pd, Os, Ir, Pt, Mn, B, P, and Re.

12. The process of claim 11 wherein the promoter comprises from about 0.001 to 20 mole percent of the total metal content.

13. The process of claim 12 wherein the promoter comprises from about 2 to 5 mole percent of the total metal content.

14. The process of claim 12 wherein the catalytically active metal is cobalt, the promoter is rhenium, wherein the combined cobalt and rhenium content is from about 10 to about 50 mole percent of the total metal, and the rhenium content is from about 0.001 to about 5 mole percent of the total metal.

15. The process of claim 12 wherein the promoter is rhenium, the combined content of cobalt, ruthenium, and rhenium is from about 10 to about 50 mole percent, and the combined content of rhenium and ruthenium is from about 0.001 to 5 mole percent.

16. The process of claim 14 wherein the matrix metal is selected from the group consisting of titanium, cerium, aluminum, a mixture of cerium and aluminum, a mixture of silicon and aluminum, and a mixture of titanium and aluminum.

17. The process of claim 15 wherein the matrix metal is selected from the group consisting of titanium, cerium, aluminum, a mixture of cerium and aluminum, a mixture of silicon and aluminum, and a mixture of titanium and aluminum.

18. A process for producing hydrocarbons by contacting a feed stream comprising hydrogen and carbon monoxide with a catalyst in a reaction zone maintained at conversion-promoting conditions effective to produce an effluent stream comprising said hydrocarbons, characterized by using a catalyst prepared by a method comprising (1) forming a catalyst gel by destabilizing an aqueous colloid comprising (a) at least one catalytic metal for Fischer-Tropsch reactions, (b) at least one colloidal oxide selected from the group consisting of cerium oxide, zirconium oxide, titanium oxide and aluminum oxide, and optionally (c) at least one alkoxide selected from the group consisting of $Al(OR)_3$, $Si(OR)_4$, $Ti(OR)_5$ and $Zr(OR)_4$, where each R is an alkyl group having from 1 to 6 carbon atoms; and (2) drying the gel.

19. The process of claim 18 wherein the catalytic metal of (a) is a combination of cobalt and ruthenium.

20. The process of claim 18 wherein the drying (2) is accomplished by vacuum drying or heating in air.

21. The process of claim 18 wherein the drying (2) is accomplished by allowing supercritical fluid to flow through the gel material.

22. The process of claim 18 wherein the catalyst preparation further comprises reduction treatment of the dried gel from (2).

* * * * *